United States Patent [19]

Hyans

[11] Patent Number: 4,459,318

[45] Date of Patent: Jul. 10, 1984

[54] METHOD FOR FORMING A SELF-LUBRICATING FILL TUBE

[75] Inventor: Thomas E. Hyans, Newport Beach, Calif.

[73] Assignee: American Hospital Supply Corporation, Evanston, Ill.

[21] Appl. No.: 501,966

[22] Filed: Jun. 10, 1983

Related U.S. Application Data

[62] Division of Ser. No. 319,340, Nov. 9, 1981, abandoned.

[51] Int. Cl.³ .......................... B05D 3/06; B05D 3/12; B05D 1/18
[52] U.S. Cl. ....................................... 427/36; 138/109; 138/145; 427/57; 427/354; 427/430.1; 604/175; 604/265; 604/266; 604/275; 604/283
[58] Field of Search ............. 427/36, 57, 393.5, 430.1, 427/235, 354; 138/109, 145; 604/175, 265, 266, 275, 283

[56] References Cited

U.S. PATENT DOCUMENTS

| | | | |
|---|---|---|---|
| 2,940,869 | 6/1960 | Graham | 427/36 |
| 2,956,899 | 10/1960 | Cline | 427/36 |
| 3,861,396 | 1/1975 | Vaillancourt et al. | 138/145 X |
| 3,919,724 | 11/1975 | Sanders et al. | 604/275 X |
| 4,043,356 | 8/1977 | Morris et al. | 604/175 X |
| 4,119,094 | 10/1978 | Micklus et al. | 604/265 X |
| 4,302,485 | 11/1981 | Last et al. | 427/57 |

*Primary Examiner*—Michael R. Lusignan
*Attorney, Agent, or Firm*—Roger A. Williams

[57] ABSTRACT

A self-lubricating fill tube comprises an extended conduit having a coating of hydrophilic polymer extending over at least a portion of an outer surface of the conduit. A method for forming the self-lubricating fill tube comprises preparing the surface of the fill tube by cleaning and irradiating the fill tube with gamma radiation in a dosage of about 0.5 Mrads. The fill tube is immersed in a ethylenically unsaturated monomer solution containing oxidizable metallic ions which initiates polymerization of the monomer onto the exposed surface of the fill tube. The fill tube is removed from the monomer solution leaving a hydrophilic polymer coating on the surface of the fill tube. The polymer coated fill tubes are rinsed with deionized water.

6 Claims, 4 Drawing Figures

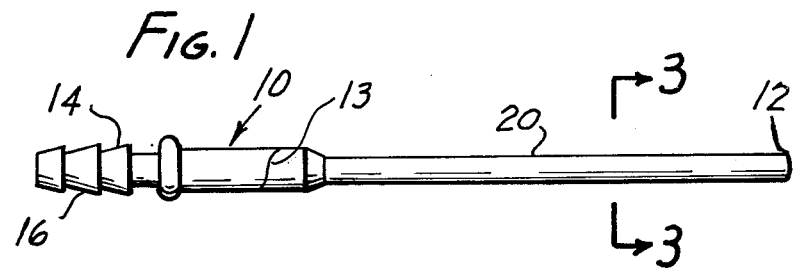
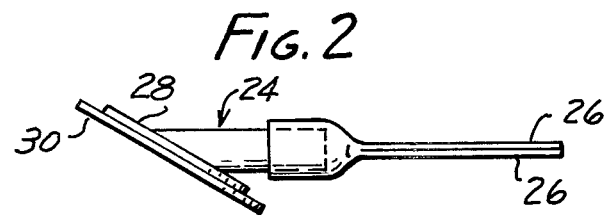
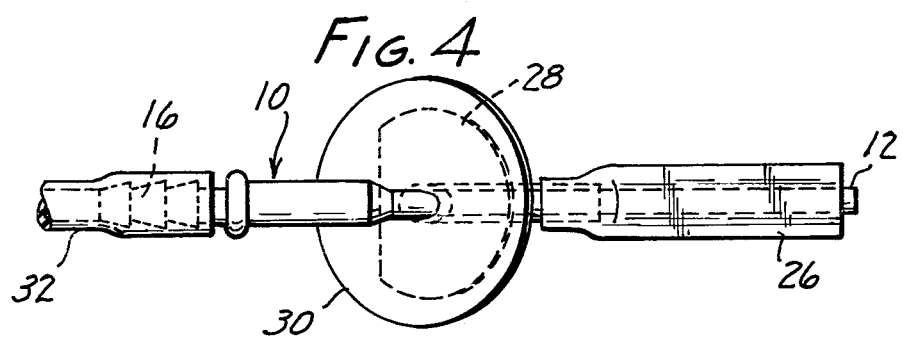
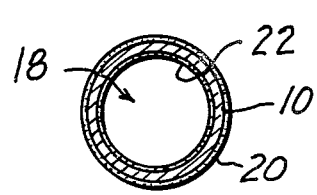

METHOD FOR FORMING A SELF-LUBRICATING FILL TUBE

This application is a division of application Ser. No. 319,340, filed Nov. 9, 1981, now abandoned.

BACKGROUND OF THE INVENTION

The invention herein is directed to a self-lubricating fill tube. In a particular aspect the self-lubricating fill tube has utility during a procedure for inflating devices through a retention valve.

In the medical field, there are many devices that are utilized which require expansion during use. Many of such devices are inflated either with a gas or liquid to bring about such expansion. The retention valves on such medical devices are constructed to permit the introduction of additional fluid and prevent the escape of the fluid contained in the device. Generally such valves are constructed of a self-sealing rubber and can have configurations such as flap or duckbill valves.

A problem with inflating medical devices is the resistive force encountered during the introduction of a fill tube to the device for delivery of the expansion fluid. The retention valves are generally constructed of rubber such that the operating valve portions of the retention valve are under pressure, which forces the rubber portions together. The pressure exerted to hold the rubber portions together contributes to a relatively high coefficient of friction to the contacting rubber surfaces. Previous fill tubes have been constructed of steel and plastics, such as teflon and polypropylene. These plastics do not significantly overcome the high coefficient of friction of the rubber surfaces through which the fill tube is inserted. Much difficulty has been encountered using teflon and polypropylene fill tubes when trying to introduce the fill tubes through the retention valves of implanted medical devices.

It would be desirable to have a fill tube constructed in such a manner that it would be readily insertable through the retention valve on inflatable medical devices.

SUMMARY OF THE INVENTION

A self-lubricating fill tube is provided by the invention herein which can be readily inserted through retention valves on devices to which a fluid is introduced. The self-lubricating fill tube herein includes an extended conduit having a coating of hydrophilic polymer extending over at least a portion of the outer surface of the conduit. The configuration of the extended conduit forming the fill tube can be any configuration suitable for insertion through a retention valve. Generally the configuration depends upon the use or the particular device and retention valve in the device. The fill tube can have a generally constant cross-sectional diameter or can have a tapered configuration with the cross-sectional diameter at the distal end being less than the cross-sectional diameter at the proximal end. In addition, the proximal end of the fill tube can have a coupling for attachment of the fill tube to suitable tubing which provides delivery of the fluid to the inflatable device.

The hydrophilic polymer coating extending over at least a portion of the surface of the fill tube provides the self-lubricating character to the fill tube. The hydrophilic polymer can be derived from a wide variety of ethylenically unsaturated monomers capable of free radical polymerization to provide hydrophilic coatings. Suitable monomers include methacrylamide, sodium methacrylate, citraconic acid, methylolacrylamide, 2-hydroxyl ethyl acrylate, potassium acrylate, sodium acrylate, calcium acrylate, cobalt acrylate, 2-acrylamido-2-methyl propane sulfonic acid, acrylamide, 2-hydroxy-ethyl methacrylate (HEMA), glycidylmethacrylate (GMA), vinly pyrrolidone, acrylic acid, methacrylic acid.

The invention herein also includes a method for forming a self-lubricating fill tube having a hydrophilic polymer coating covering at least a portion of the surface of the fill tube. The method is conducted by first cleaning the surface of a plastic fill tube and then irradiating the fill tube with actinic radiation to provide a surface sufficient for initiating polymerization of the monomer. Such actinic radiation can be gamma radiation. Following irradiation, the fill tube is introduced to a bath containing the monomer. While the fill tube is immersed in the bath, the bath is heated to a temperature sufficient to initiate polymerization of the monomer. The fill tube is removed from the bath and rinsed with deionized water, leaving a hydrophilic lubricious coating of polymer on the exposed surface of the fill tube.

BRIEF DESCRIPTION OF THE DRAWINGS

The invention herein will be more fully understood with reference to the following description and accompanying drawings wherein:

FIG. 1 is a cross-sectional elevational view of a self-lubricating fill tube;

FIG. 2 is a cross-sectional elevational view of a closed retention valve;

FIG. 3 is a cross-sectional view taken along line 3—3 of FIG. 1; and

FIG. 4 illustrates the self-lubricating fill tube of FIG. 1 inserted through a retention valve, such as FIG. 2.

DETAILED DESCRIPTION OF THE INVENTION

The self-lubricating fill tube is described herein with regard to the accompanying drawings. With regard to FIG. 1, a fill tube 10 is shown having a distal end 12 and a proximal end 14. The fill tube can have any desired configuration, but generally has a configuration which provides a smaller cross-sectional diameter at the distal end of the fill tube than the cross-sectional diameter at the proximal end of the fill tube. Such a configuration can be realized by the design shown in FIG. 1, or the fill tube can have a generally tapered shape with the fill tube tapering from the proximal end to the distal end.

At the proximal end of the fill tube there can be provided a connector 16. The connector provides for adapting the fill tube to tubing, such as a flexible tubing connected to a fluid supply source.

The fill tube herein can be constructed of a polymeric material. Examples of suitable polymeric materials include both synthetic and natural polymers, such as polyethylene, polypropylene, polymethylmethacrylate, silicone rubber, polycarbonates, polyesters, natural and synthetic rubbers, polyurethanes, polyamides, cured epoxy resins, cellulosics, polyvinyl chloride formulations, polystyrene, natural fibers and various copolymers.

The fill tube 10 is a tube or conduit having at least one lumen 18 such as shown in FIG. 4. In view thereof, the invention herein is not meant to be limited to fill tubes but is meant to encompass any tubular conduit, e.g. catheters.

Also shown in FIG. 4 is the lubricious coating on the exposed surfaces of the fill tube. A lubricious coating 20 on the outer exposed surface of the fill tube provides the self-lubricating characteristic to the fill tube. The lubricious coating extends over at least a portion of the exposed surface of the fill tube. For example, the lubricious coating can extend from the distal end 12 to the area generally designated as 13 in FIG. 1 of the fill tube. Of course, the lubricious coating can extend over the entire outer surface. A lubricious coating 22 can also be provided on the inside exposed surface of the fill tube. The lubricious coating 22 on the inner surface of the fill tube does not affect the self-lubricating character of the fill tube for the purpose of inserting the fill tube through a retention valve. This lubricious coating 22 on the inner surface is a result of the process herein for applying the polymeric self-lubricating coating to the fill tube. The lubricious coating 22 does facilitate the insertion of a tube through the lumen 18.

The lubricious coatings 22 and 24 provided on the fill tube can be the polymerization product of a monomer derived from a wide variety of ethylenically unsaturated compounds. Suitable monomers which can be used include methacrylamide, sodium methacrylate, citraconic acid, methylolacrylamide, 2-hydroxy-ethyl acrylate, potassium acrylate, sodium acrylate, calcium acrylate, cobalt acrylate, 2-acrylamido-2-methyl propane sulfonic acid, acrylamide, 2-hydroxy-ethyl methacrylate (HEMA), glycidylmethacrylate (GMA), vinyl pyrrolidone, acrylic acid, and methacrylic acid.

The fill tube herein having the self-lubricating quality can be readily inserted through a retention valve, such as retention valve 24. The retention valve 24 shown in FIG. 2 is a retention valve having general characteristics common to many retention valves. Namely, the retention valve is a self-sealing rubber retention valve. The retention valve 24 has two resilient rubber flaps 26. Such an arrangement is commonly referred to as a "duckbill" flap valve. Rather than being two separate flaps 26, the two flaps 26 could be connected at their edges. The resilient valve would then have a flattened rubber tubing appearance with the lumen extending through the tubing being closed except when a fill tube is inserted therethrough.

The retention valve can have a base 28 which can be attached to the wall 30 of a medical device, which medical device is generally used in an inflated condition. For example, the medical device can be a mammary prosthesis, skin expander, and the like.

The self-lubricating fill tube is shown inserted through a retention valve in FIG. 4. To insert the fill tube through the retention valve, the distal end 12 of the fill tube is introduced through a slit on the base of the retention valve into and through the body of the retention valve. The fill tube is then introduced to a greater depth through the flaps 26 of the retention valve. As the fill tube is inserted through the flaps, little or substantially reduced frictional force is encountered due to the hydrophilic coating on the fill tube. The distal end of the fill tube is inserted through the retention valve until it protrudes a sufficient distance for introducing fluid to the medical device to be inflated. The fluid for inflating the medical device can then be introduced through provided tubing 32 attached to the connector at the proximal end of the fill tube. The tubing 32 can be connected to a fluid supply (not shown). After the device is inflated to the desired dimensions, the fill tube can be withdrawn from the retention valve, again without encountering any significant friction in view of the lubicious hydrophilic coating on the fill tube.

The fill tube herein is constructed of any suitable polymeric material either synthetic or natural polymer, such as polyethylene, polypropylene, polymethylmethacrylate, silicone rubber, polycarbonates, polyesters, natural and synthetic rubbers, polyurethane, polyamide, cured epoxy resins, cellulosics, polyvinyl chloride formulations, polystyrene, natural fibers and various copolymers. The fill tube is constructed of such a polymeric material in a molding process to provide the initial shape and configuration to the fill tube. Generally once constructed of such material the surface is hydrophobic. Thus, the surface of the fill tube needs to be treated to enable the hydrophilic polymer to adhere to it.

The fill tube is first treated by cleaning the surface. The surface of the fill tubes is cleaned to provide a substantially clean surface on which the polymer coating can adhere. The surface of the fill tubes can be cleaned using fluorocarbon vapor degreasing techniques. The fill tube is sprayed with a fluorocarbon, such as commercially available under the trademark Freon of E. I. DuPont de Nemours Co., while in a field of sonic waves generated by ultrasonic sound generators. The fill tube is sprayed with a sufficient quantity of liquid flurocarbon while in the ultrasonic field. After the fill tubes have been exposed to the liquid fluorocarbon spray and ultrasonic sound waves, the tubes are raised to an area of vapor condensation out of the liquid spray. The tubes are allowed to be rinsed by the condensing fluorocarbon vapors. The fluorocarbon is permitted to conpletely evaporate from the fill tubes. The surfaces of the fill tubes after such a degreasing technique are sufficiently clean to enable coating thereof which the monomer and resulting polymer.

The fill tubes are irradiated with actinic radiation, such as gamma radiation, to a total dosage suitable to form peroxide on the surface. A suitable source of such gamma radiation is cobalt-60. A preferred radiation dosage for such cobalt-60 gamma radiation is at least 0.5 Mrad, and more preferably at least 2.5 Mrad. Although described using gamma radiation, the high energy ionizing radiation can take the form of gamma rays or high energy electrons produced by a particle accelerator.

The surface of the fill tube is peroxidized by the radiation when such irradiation is conducted in the presence of available oxygen. That is, peroxide groups form on the surface, which peroxide groups include hyperoxides. The peroxide groups are relatively unstable and decompose readily upon heating to form peroxide free radicals. The peroxide free radicals interact with the monomer to initiate polymerization. If the coating step is not to be performed immediately after the irradiating step, it is preferable to maintain the irradiated fill tubes at a sufficiently low temperature to substantially avoid the formation of peroxide free radicals. Such a temperature can be about 0° centigrade.

Coating of the fill tubes with the hydrophilic polymer can be performed using any suitable coating technique. A preferred coating technique is conducted by forming a solution of the monomer and dipping the fill tubes into the monomer solution which is held at a sufficiently high temperature to enable the formation of free radical peroxides on the surface of the fill tubes. The formation of the free radical peroxides initiate the polymerization process and bonding of the formed polymers to the surface of the fill tube.

The monomer solution can be formed by dissolving a suitable amount of the monomer in sufficient deionized water. A free radical scavenger is also added to the solution in order to inhibit homopolymerization of the monomer. The free radical scavenger or homopolymerization inhibiting agent can be any suitable metal capable of being oxidized from a lower valence state to a higher valence state. Metals such as iron, cobalt, manganese, molybdenum, tin and indium can be used to be oxidized from their reduced (-ous) state to their oxidized (-ic) state. Any suitable metal salt can provide the source of the metallic ions and in the case of ferrous ions, a preferred source is ferrous ammonium sulfate, although other ferrous salts, such as ferrous sulfate, ferrous chloride, ferrous iodide and ferrous bromide can be effectively employed.

The solution of monomer is generally an aqueous solution of the monomer and oxidizable metal. This solution is heated and the temperature maintained at a sufficient temperature to provide free radical polymerization of the monomer when a peroxide free radical is introduced. For a polypropylene fill tube the temperature can be about 75° C. The peroxide free radical is introduced by immersing a fill tube having available peroxides on its surface into the monomer solution. The temperature of the solution is sufficient to decompose the available peroxides to peroxide free radicals. The fill tube is dipped or immersed into the heated solution to any desired depth depending upon the amount of coating to be imparted to the fill tube. Depending upon the end use for the fill tube and the retention valve through which it is to be inserted, the fill tube can be dipped to any depth within the monomer solution to provide the hydrophilic coating over any portion of the surface of the fill tube. For example, in many instances it is desirable to provide the hydrophilic coating over a substantial portion of the surface of the fill tube, such as over that portion of the fill tube up to the area 13 for a fill tube as shown in FIG. 1.

When the fill tube is immersed into the monomer solution, the peroxides on the surface of the fill tube become heated by the warm monomer bath such that the peroxides decompose to form peroxide free radicals. The peroxide free radicals initiate polymerization of the monomer and bond the formed polymer onto the surface of the fill tube. In such an environment, the fill tube obtains a substantially uniform coating of the polymer over its exposed surface. The exposed surface of the fill tube includes the inner surface of the lumen extending through the fill tube. The inner surface also can be peroxidized by the irradiating step such that, upon immersion of the fill tube into the monomer bath, any monomer flowing into the lumen, such as through capillary action, can react to form a polymer coating on the inner surface. A cross section of a fill tube is shown in FIG. 3 illustrating an outer lubricious coating 20 and an inner lubricious coating 22 on the fill tube 10.

The self-lubricating fill tube and method for its production are illustrated in the following example which details the process for the production of a working embodiment of the self-lubricating fill tube described herein.

EXAMPLE

A fill tube having the general configuration as shown in FIG. 1 and constructed of polypropylene was prepared for coating with a lubricious coating of a hydrophilic polymer.

The fill tube was placed in a cleaning basket within an ultrasonic sound chamber. The ultrasonic sound generators were switched on and the fill tube was sprayed with a liquid Freon for 3 minutes. The fill tube was agitated to insure that all surfaces of the fill tube were exposed to the liquid Freon. The fill tube was raised above the liquid Freon level to an area of vapor condensation. The fill tube was rinsed by the condensing vapors for an additional 3 minutes. The fill tube was removed from the chamber and the Freon permitted to evaporate completely.

The fill tube was then irradiated with gamma radiation from a cobalt 60 source to provide a total dosage of 2.5 Mrad. After irradiating the fill tube, at least within one hour thereafter, the fill tube was placed in an insulated container under a carbon dioxide atmosphere. The fill tube was cooled within the insulated container. The fill tube was transferred to a refrigeration chamber for storage prior to immersing the fill tube in the monomer solution. The fill tube was refrigerated at a temperature of about 0° centigrade.

A monomer solution was prepared in a vessel having a cover. The vessel was provided with a gas inlet and thermometer for monitoring temperature. To the vessel was added 6 liters±0.05 liters of purified water. A flow rate of nitrogen was introduced to the vessel at a rate of 20 standard cubic feet per hour (SCFH)±5 SCFH. This nitrogen flow rate was permitted to continue for 2 hours.

To the vessel was then added 668.5 grams±0.5 grams of acrylamide. About 15 minutes after the addition of the acrylamide, 16.71 grams±0.05 grams of ferrous ammonium sulfate was added to the reaction vessel. Following the addition of the ferrous ammonium sulfate and permitting the ferrous ammonium sulfate to thoroughly intermix and dissolve for about 15 minutes, heat was applied to the vessel to raise the temperature of the solution to about 75° centigrade±3° centigrade.

The nitrogen flow rate was reduced to 10 SCFH±5 SCFH, but was restored to 20 SCFH±5 SCFH before the first fill tube was placed in the solution.

During the coating step, the temperature of the monomer solution was maintained at 75° C.±3° C. except for any transitory drop in temperature to no less than 70° C. after introduction of the cold fill tube into the monomer solution. The temperature was monitored to insure that the duration of any deviation from the specified temperature was no more than 5 minutes.

The nitrogen flow rate was also monitored to insure that the flow rate was 20 SCFH±5 SCFH during the polymer coating operation.

The fill tube was maintained in the monomer solution for 45 minutes±15 minutes. This time was sufficient to provide grafting of the monomer onto the fill tube.

The fill tube was removed from the monomer solution and rinsed with deionized water. Both the outside surface and the inner surface of the fill tube were washed. The lumen of the fill tube was cleaned with clean pressurized air to remove any water that was present. The fill tube was placed in an oven and heated to 50° C.±5° C. for 2 hours±0.5 hours.

The resulting fill tube had a lubricious polymer coating on its surface. The fill tube had a self-lubricating nature in that the polymer (polyacrylamide) exhibited hydrophilic properties. The fill tube was easily inserted through a retention valve of a mammary prosthesis.

I claim:

1. A method for forming a self-lubricating fill tube which can be readily inserted through a retention valve, the method comprising the steps of:
   (a) cleaning the surface of a fill tube by exposing the fill tube to a fluorocarbon in an ultrasonic sound field;
   (b) irradiating the fill tube with gamma radiation to provide a radiation dosage of about at least 0.5 Mrad;
   (c) immersing the fill tube in a solution comprising an ethylenically unsaturated monomer and oxidizable metal ion at a temperature of about 75° C. for about 45 minutes under a nitrogen atmosphere;
   (d) rinsing the fill tube with deionized water leaving a hydrophilic lubricious coating of the polymerized monomer on the surface of the fill tube.

2. A method as recited in claim 1 wherein the ethylenically unsaturated monomer comprises a monomer selected from the group consisting of methacrylamide, sodium methacrylate, citraconic acid, methylolacrylamide, 2-hydroxy-ethyl acrylate, potassium acrylate, sodium acrylate, calcium acrylate, cobalt acrylate, 2-acrylamido-2-methyl propane sulfonic acid, acrylamide, 2-hydroxy-ethyl methacrylate, glycidylmethacrylate, vinyl pyrrolidone, acrylic acid, and methacrylic acid.

3. A method as recited in claim 2 wherein the ethylenically unsaturated monomer comprises acrylamide.

4. A method as recited in claim 1 wherein after the irradiating step the method further comprises the step of cooling the fill tube to a temperature of about 0° centigrade and holding the fill tube at such temperature until the fill tube is immersed in the monomer solution.

5. A method as recited in claim 1 wherein the rinsing step comprises rinsing the outer surface and lumen of the fill tube.

6. A method as recited in claim 1 further comprising the step of drying the fill tube after rinsing.

* * * * *